United States Patent [19]

Ohtaka et al.

[11] Patent Number: 4,797,400

[45] Date of Patent: Jan. 10, 1989

[54] PIPERAZINE COMPOUNDS AND ANTI-ULCER COMPOSITION CONTAINING THE SAME

[75] Inventors: Hiroshi Ohtaka; Kenji Yoshida, both of Osaka; Kenji Sukuzi, Nara; Koichi Shimohara, Neyagawa; Sigeru Tajima; Keizo Ito, both of Osaka, all of Japan

[73] Assignee: Kanebo, Ltd., Japan

[21] Appl. No.: 62,573

[22] Filed: Jun. 16, 1987

[30] Foreign Application Priority Data

Jun. 23, 1986 [JP] Japan .................. 61-147789

[51] Int. Cl.$^4$ .................. A61K 31/495; C07D 295/14
[52] U.S. Cl. ..................... 514/255; 544/399
[58] Field of Search ............ 544/399; 514/255

[56] References Cited

U.S. PATENT DOCUMENTS

| | | | |
|---|---|---|---|
| 2,907,764 | 10/1959 | Voegtli et al. | 544/399 |
| 2,996,506 | 8/1961 | Gold-Aubert | 544/399 |
| 3,025,297 | 3/1962 | Robinson | 544/399 |
| 3,389,138 | 6/1968 | Larizza et al. | 544/399 |
| 3,573,291 | 3/1971 | Fauran et al. | 544/399 |
| 3,594,384 | 7/1971 | Stachel et al. | 544/399 |
| 3,658,821 | 4/1972 | Fauran et al. | 544/399 |

FOREIGN PATENT DOCUMENTS

| | | | |
|---|---|---|---|
| 6113771 | 9/1981 | Japan | 544/399 |
| 1184408 | 3/1970 | United Kingdom | 544/399 |

Primary Examiner—Donald G. Daus
Assistant Examiner—Cecilia Shen
Attorney, Agent, or Firm—Wegner & Bretschneider

[57] ABSTRACT

Novel piperazine compounds of the formula:

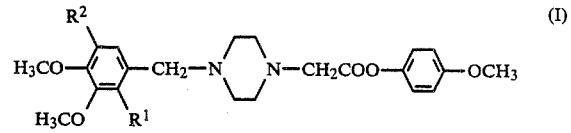

(I)

wherein either one of $R^1$ and $R^2$ is methoxy group and another is hydrogen atom, or a pharmaceutically acceptable acid addition salt thereof, which have excellent anti-peptic ulcer activities with potent activity for promoting the action of the defensive factor, and hence are useful as an anti-ulcer agent for the prophylaxis and treatment of peptic ulcers.

6 Claims, No Drawings

PIPERAZINE COMPOUNDS AND ANTI-ULCER COMPOSITION CONTAINING THE SAME

This invention relates to novel piperazine compounds and an anti-ulcer composition containing the compound as an active ingredient. More particularly, it relates to novel piperazine compounds of the formula:

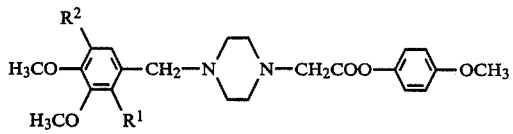

wherein either one of $R^1$ and $R^2$ is methoxy group and another is hydrogen atom, or a pharmaceutically acceptable acid addition salt thereof, and an anti-ulcer composition for the prophylaxis and treatment of peptic ulcers, which contains as an active ingredient the above compound or a pharmaceutically acceptable acid addition salt thereof.

PRIOR ART

Peptic ulcers are classified into duodenal ulcer and gastric ulcer based on the region of the disease. It is considered that these ulcers will be induced by unbalance between the aggressive factor such as gastric acid or pepsin and the resistance of gastrointestinal mucosa (i.e. defensive factor) against the aggressive factor, and that the gastric ulcer is mainly induced by weakening of the defensive factor. Accordingly, for the purpose of the treatment and prophylaxis of the gastric ulcer, it is desirable to use an anti-ulcer agent which has particularly excellent activity for promoting the action of the defensive factor.

There has been known various anti-ulcer agents which have activities for promoting the action of the defensive factor, and as a representative example of these agents, cetraxate hydrochloride of the following formula has clinically widely been used.

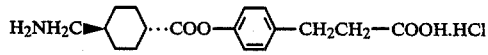

However, the known anti-ulcer agents have not necessarily sufficient activity for promoting the action of the defensive factor, and hence, it has hitherto been desired to develop an anti-ulcer agent having more potent activity for promoting the action of the defensive factor.

BRIEF DESCRIPTION OF THE INVENTION

The present inventors have intensively studied as to various piperazine derivatives for the purpose of developing the desired anti-ulcer agent having such desired activities, and have found that the novel piperazine compounds of the above formula (I) and a pharmaceutically acceptable acid addition salt thereof have the desired excellent activities.

An object of the invention is to provide novel piperazine compounds of the formula (I) and a pharmaceutically acceptable acid addition salt thereof which have excellent anti-ulcer activity with potent activity for promoting the action of the defensive factor. Another object of the invention is to provide processes for preparing the novel piperazine compounds as set forth above. A further object of the invention is to provide an anti-ulcer composition for the prophylaxis and treatment of peptic ulcers which contains as an active ingredient the piperazine compound of the formula (I) or a pharmaceutically acceptable acid addition salt thereof. These and other objects and advantages of the invention will be apparent to those skilled in the art from the following description.

DETAILED DESCRIPTION OF THE INVENTION

The compounds of this invention are the novel piperazine compounds of the formula (I) and a pharmaceutically acceptable acid addition salt thereof. Preferred compounds are as follows:

1-[(4-Methoxyphenoxy)carbonylmethyl]-4-(2,3,4-trimethoxybenzyl)piperazine

1-[(4-Methoxyphenoxy)carbonylmethyl]-4-(3,4,5-trimethoxybenzyl)piperazine

The pharmaceutically acceptable acid addition salts of the compounds (I) include inorganic acid addition salts such as hydrochloride, hydrobromide, sulfate, etc. and organic acid addition salts such as maleate, fumarate, succinate, citrate, etc.

The compounds (I) of this invention can be prepared by various methods. Preferred method is, for example, a method as shown by the following reaction scheme:

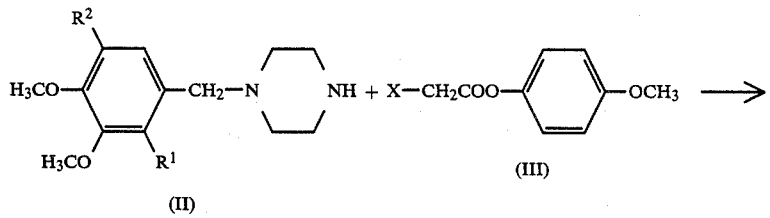

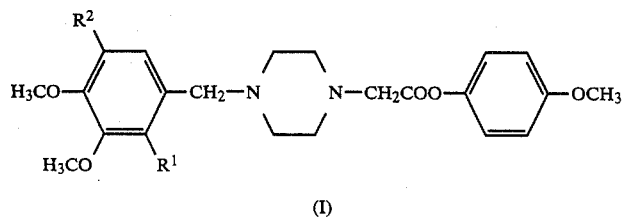

wherein X is a halogen atom, and $R^1$ and $R^2$ are as defined above.

That is, the compounds (I) of this invention can be prepared by reacting a known compound (II) or an acid addition salt thereof with 1 to 1.5 equivalent amount of a compound (III) in the presence of a base in a solvent.

The solvent includes aromatic hydrocarbons (e.g. benzene, toluene, etc.), chlorinated aliphatic hydrocarbons (e.g. chloroform, trichloroethane, etc.), alcohols (e.g. ethanol, isopropanol, etc.), acetonitrile, methyl ethyl ketone, 1,4-dioxane, N,N-dimethylformamide, dimethylsulfoxide, and the like. The base includes inorganic bases such as potassium carbonate, sodium carbonate, potassium hydrogen carbonate, sodium hydrogen carbonate, etc., and organic bases such as triethylamine, N,N-dimethylaniline, etc. These bases are preferably used in an amount of 1 to 1.5 equivalent to the amount of compound (II), and when the compound (II) is used in the form of an acid addition salt thereof, the amount of the bases is preferably in the range of 3 to 5 equivalents to the amount of the acid addition salt of the compound (II). The reaction is usually carried out at a temperature of from room temperature to a boiling point of the solvent for a period of 2 to 30 hours.

The compounds (I) of this invention prepared by the above method can be isolated and purified from the reaction mixture in a usual manner, preferably in the form of an acid addition salt thereof. Optionally, the acid addition salt may be converted into the corresponding free base, or alternatively, may be converted into an other acid addition salt, in a usual manner.

The compounds (I) and the pharmaceutically acceptable acid addition salts of this invention have potent activity for promoting the action of the defensive factor as mentioned hereinafter and are useful for the prophylaxis and treatment of peptic ulcers, as an anti-ulcer agent.

The compounds of this invention are administered to patients preferably in oral route. The compounds of this invention are preferably used in the form of conventional preparations for oral administration, such as tablets, granules, fine granules, powders, and the like by admixing with conventional pharmaceutically acceptable carriers or diluents, for example, excipients (e.g. lactose, synthetic aluminum silicate, glucose, mannitol, etc.), disintegrators (e.g. carboxymethyl cellulose, sodium alginate, etc.), lubricants (e.g. magnesium stearate, talc, etc.), and binders (e.g. corn starch, polyvinylpyrrolidone, etc.), and capsules which are prepared by filling the granules, fine granules, or powders into capsules.

The dose of the compounds of this invention for oral administration is usually in the range of 0.2 to 20 mg/kg per day for adult, which may be administered at one time or by dividing in 2 to 3 times per day.

The compounds of this invention have potent activity for promoting the action of the defensive factor. The activity can be evaluated by the defensive action against ulcer induced by ethanol (e.g. inhibitory effect on ethanol-induced gastric ulcer) [cf. Hara, Nobuyuki et al., Pharmacometrics, 29, 557 (1985)]. As shown in the experiment hereinafter, the compounds of this invention showed excellent activity for promoting the action of the defensive factor (cf. Experiment 1 hereinafter).

Moreover, the compounds of this invention show also excellent anti-ulcer activity in case of indomethacin-induced gastric ulcer and stress-induced gastric ulcer (i.e. water-immersion stress-induced gastric ulcer) which are usually used in evaluation of anti-ulcer activity (cf. Experiments 2 and 3 hereinafter).

Besides, the compounds of this invention have a low toxicity (cf. Experiment 4 hereinafter).

Thus, the compounds of this invention are useful as an anti-ulcer agent having a potent activity for promoting the action of the defensive factor with high safety.

The activities of the compounds of this invention are illustrated by the following experiments.

Experiment 1

Inhibitory effect on ethanol-induced gastric ulcer:
Test compounds
(1) Compound 1 of this invention:
1-[(4-Methoxyphenoxy)carbonylmethyl]-4-(2,3,4-trimethoxybenzyl)piperazine dihydrochloride [compound in Example 1-(1)]
(2) Compound 2 of this invention:
1-[(4-Methoxyphenoxy)carbonylmethyl]-4-(3,4,5-trimethoxybenzyl)piperazine difumarate monohydrate [compound in Example 2-(1)]
(3) Reference compound:
Cetraxate hydrochloride
Method Male Sprague-Dawley (SD) rats (weighing 180–220 g, 8 weeks age, 16 rats per group) were fasted for 24 hours, and to the rats was orally administered the test compound in the form of a solution in distilled water or a suspension in 1% aqueous gum arabic. After 30 minutes, ethanol (99.5%, 1 ml) was orally administered to the rats in the same manner as described by Robert et al. [cf. Gastroenterology, 77, 433 (1979)]. One hour after the administration of ethanol, the rats were sacrificed under ether anesthesia, and the stomach was removed. Into the stomach was poured 1% formalin (12 ml), and then the stomach was immersed in 1% formalin for 15 minutes. The stomach was cut along the greater curvature, and the length (mm) of each ulcer occured on the fundic mucosa was measured with a dissecting microscope. Sum of the length of ulcers in each rat was used as the ulcer index in each rat. In control rats to which no test compound was administered, the ulcer index was determined likewise, and the mean value (mean ulcer index) was calculated. From these data, there was calculated the ratio of the ulcer index in rats administered with the test compound to the mean ulcer index in the control rats. A dose-response curve was drawn based on the ratio thus obtained and the dose of test compounds, and therefrom, the 50% effective dose ($ED_{50}$) was determined.

Results

The test results are shown in Table 1.

Experiment 2

Inhibitory effect on water-immersion stress-induced gastric ulcer:
Test compounds
The same as used in Experiment 1.
Method Male SD rats (weighing 190–230 g, 8 weeks age, 16 rats per group) were fasted for 24 hours, and to the rats was orally administered the test compound in the form of a solution in distilled water or a suspension in 1% aqueous gum arabic. After 15 minutes, the rats were immersed vertically to the height of the xiphoid of the rats in water bath at 23° C. within a stress cage in the same manner as described by Takagi et al. [cf. Japanese Journal of Pharmacology, 18, 9 (1968)]. After 17 hours, the rats were sacrificed under ether anesthesia and the stomach was removed. The stomach was treated with formalin and the ulcer index as well as $ED_{50}$ were determined in the same manner as described in Experiment 1.

Results

The test results are shown in Table 1.

Experiment 3

Inhibitory effect on indomethacin-induced gastric ulcer:

Test compounds

The same as used in Experiment 1.

Method

It was done in the same manner as described by Okabe et al. [cf. Digestive Diseases and Science, 28, 1034 (1983)].

That is, male SD rats (weighing 180–220 g, 8 weeks age, 16 rats per group) were fasted for 24 hours, and to the rats was orally administered the test compound in the form of a solution in distilled water or a suspension in 1% aqueous gum arabic. After 15 minutes, to the rats was subcutaneously administered indomethacin (30 mg/kg) in the form of a solution in 3% aqueous sodium hydrogen carbonate solution. After 5 hours, the rats were sacrificed under ether anesthesia and the stomach was removed. The stomach was treated with formalin and the ulcer index as well as $ED_{50}$ were determined in the same manner as described in Experiment 1.

Results

The test results are shown in Table 1.

Experiment 4

Acute toxicity:

Test compounds

The same as used in Experiment 1.

Method

To male ddY mice (weighing 18–22 g, 4 weeks age, 5% mice per group) fasted overnight was orally administered the test compound in the form of a solution in distilled water or a suspension in 1% aqueous gum arabic. Thereafter, the death of mice was observed for 7 days. From the number of dead mice, $LD_{50}$ was determined in the same manner as Weil's method.

Results

The test results are shown in Table 1.

EXAMPLE 1

Preparation of
1-[(4-methoxyphenoxy)carbonylmethyl]-4-(2,3,4-trimethoxybenzyl)piperazine and acid addition salts thereof (1)
1-[(4-Methoxyphenoxy)carbonylmethyl]-4-(2,3,4-trimethoxybenzyl)piperazine dihydrochloride A mixture of 1-(2,3,4-trimethoxybenzyl)piperazine dihydrochloride (prepared by the method disclosed in Japanese Patent First Publication (Kokai) No. 32889/1973) (17.0 g), 4-methoxyphenyl chloroacetate (prepared by the method disclosed in U.S. Pat. No. 3,657,318) (10 g), potassium carbonate (27.6 g) and N,N-dimethylformamide (200 ml) is stirred at 50° C. for 4 hours. To the reaction mixture is added water (400 ml), and the mixture is extracted with chloroform (400 ml). The organic layer is washed with water twice and dried over anhydrous magnesium sulfate. The solvent is distilled off under reduced pressure to give crude 1-[(4-methoxyphenoxy)carbonylmethyl]-4-(2,3,4-trimethoxybenzyl)piperazine (free base) (20 g) as an oily substance. This crude free base (20 g) is dissolved in ethanol (100 ml) and thereto is added a solution of hydrochloric acid in ethanol (10% w/w) (50 ml) and the precipitated crystals are separated by filtration. The crystals are recrystallized from methanol to give 1-[(4-methoxyphenoxy)carbonylmethyl]-4-(2,3,4-trimethoxybenzyl)piperazine dihydrochloride (11.5 g) as colorless crystals.

M.p. 223°–227° C. (decomp.)

NMR (DMSO-$d_6$) δ: 3.3–3.7 (m, 8H), 3.76 (s, 3H), 3.78 (s, 3H), 3.83 (s, 3H), 3.89 (s, 3H), 4.28 (br, 2H), 4.37 (br, 2H), 6.89 (d, J=8 Hz, 1H), 6.98 (d, J=9 Hz, 2H), 7.16 (d, J=9 Hz, 2H), 7.44 (d, J=8 Hz, 1H)

Elementary analysis for $C_{23}H_{30}N_2O_6 \cdot 2HCL$ Calcd. (%): C,54.88; H,6.41; N,5.56 Found (%): C,54.88; H,6.50; N,5.68

Crude free base as prepared in the same manner as described above is treated with fumaric acid or maleic acid in a usual manner, and the crystals thus obtained are recrystallized to give the corresponding acid addition salts, the solvent for recrystallization and properties of which are shown below.

TABLE 1

| Test compounds | Inhibitory effect on ethanol-induced gastric ulcer $ED_{50}$ (mg/kg, p.o.) | Inhibitory effect on water-immersion stress-induced gastric ulcer $ED_{50}$ (mg/kg, p.o.) | Inhibitory effect on indomethacin-induced gastric ulcer $ED_{50}$ (mg/kg, p.o.) | Acute toxicity $LD_{50}$ (mg/kg, p.o.) |
| --- | --- | --- | --- | --- |
| Compound 1 of this invention | 27 | 88 | 10 | 4,200 |
| Compound 2 of this invention | 30 | 123 | 11 | 4,800 |
| Reference compound | 112 | >1,000 | 361 | >8,000 |

The above results show that the compounds of this invention are effective as an anti-ulcer agent with high safety.

The present invention is illustrated by the following Examples.

(2)
1-[(4-Methoxyphenoxy)carbonylmethyl]-4-(2,3,4-trimethoxybenzyl)piperazine monofumarate Solvent for recrystallization: ethanol Property: colorless crystals M.p. 150°–154° C. (decomp.)

NMR (DMSO-$d_6$) 2.4–2.8 (m, 8H), 3.50 (s, 2H), 3.54 (s, 2H), 3.74 (s, 6H), 3.78 (s, 3H), 3.79 (s, 3H), 6.62 (s,

2H), 6.78 (d, J=9 Hz, 1H), 6.93 (d, J=9 Hz, 2H), 7.02 (d, J=9 Hz, 1H), 7.06 (d, J=9 Hz, 2H)

Elementary analysis for $C_{23}H_{30}N_2O_6 \cdot C_4H_4O_4$: Calcd. (%): C,59.33; H,6.27; N,5.13 Found (%): C,59.23; H,6.33; N,5.11

(3)
1-[(4-Methoxyphenoxy)carbonylmethyl]-4-(2,3,4-trimethoxybenzyl)piperazine dimaleate Solvent for recrystallization: ethanol
Property: colorless crystals
M.p. 128°–132° C.

NMR (DMSO-d$_6$) δ: 2.7–3.3 (m, 8H), 3.65 (s, 2H), 3.75 (s, 3H), 3.79 (s, 3H), 3.84 (s, 3H), 3.88 (s, 3H), 4.21 (s, 2H), 6.16 (s, 4H), 6.90 (d, J=9 Hz, 1H), 6.95 (d, J=8 Hz, 2H), 7.08 (d, J=8 Hz, 2H), 7.21 (d, J=9 Hz, 1H)

Elementary analysis for $C_{23}H_{30}N_2O_6 \cdot 2C_4H_4O_4$: Calcd. (%): C,56.19; H,5.78; N,4.23 Found (%): C,55.99; H,5.89; N,4.42

Besides, the purified free base is prepared as follows:

(4)
1-[(4-Methoxyphenoxy)carbonylmethyl]-4-(2,3,4-trimethoxybenzyl)piperazine (free base)

The 1-[(4-methoxyphenoxy)carbonylmethyl]-4-(2,3,4-trimethoxybenzyl)piperazine dihydrochloride (15 g) obtained above is added to a 5% aqueous potassium carbonate solution (70 ml), and the produced oily substance is extracted with chloroform (150 ml). The chloroform layer is dried over anhydrous magnesium sulfate, and the solvent is distilled off under reduced pressure. The residue is recrystallized from a mixture of ethyl acetate and n-hexane to give 1-[(4-methoxyphenoxy)carbonylmethyl]-4-(2,3,4-trimethoxybenzyl)piperazine (6.1 g).

M.p. 68°–71° C.

NMR (CDCl$_3$) δ: 2.5–2.8 (m, 8H), 3.44 (s, 2H), 3.52 (s, 2H), 3.76 (s, 3H), 3.84 (s, 3H), 3.87 (s, 3H), 3.88 (s, 3H), 6.63 (d, J=9 Hz, 1H), 6.86 (d, J=10 Hz, 2H), 7.00 (d, J=9 Hz, 1H), 7.01 (d, J=10 Hz, 2H)

Elementary analysis for $C_{23}H_{30}N_2O_6$: Calcd. (%): C,64.17; H,7.02; N,6.51 Found (%): C,64.15; H,7.03; N,6.45

EXAMPLE 2

Preparation of 1-[(4-methoxyphenoxy)carbonylmethyl]-4-(3,4,5-trimethoxybenzyl)piperazine and acid addition salts thereof

(1)
1-[(4-Methoxyphenoxy)carbonylmethyl]-4-(3,4,5-trimethoxybenzyl)piperazine difumarate monohydrate A mixture of 1-(3,4,5-trimethoxybenzyl)piperazine dihydrochloride (prepared by the method disclosed in Belgian Pat. No. 560,330) (50 g), 4-methoxyphenyl chloroacetate (prepared by the method disclosed in U.S. Pat. No. 3,657,318) (33 g), sodium hydrogen carbonate (49 g) and acetonitrile (700 ml) is stirred at 60° C. for 3 hours. The reaction mixture is filtered, and the filtrate is concentrated under reduced pressure to give crude 1-[(4-methoxyphenoxy)carbonylmethyl]-4-(3,4,5-trimethoxybenzyl)piperazine (free base) (60 g) as an oily substance. This crude free base (60 g) is dissolved in a mixture of water (200 ml) and acetonitrile (50 ml) and thereto is added fumaric acid of about 2 moles (41 g) to 1 mole of the free base, and the mixture is heated. After the reaction mixture is allowed to cool at room temperature, the precipitated crystals are separated by filtration and recrystallized from a mixture of water and acetonitrile to give 1-[(4-methoxyphenoxy)carbonylmethyl]-4-(3,4,5-trimethoxybenzyl)piperazine difumarate monohydrate (73.5 g) as colorless crystals.

M.p. 163°–167° C.

NMR (DMSO-d$_6$) δ: 2.5–2.8 (m, 8H), 3.52 (s, 2H), 3.64 (s, 5H), 3.75 (s, 3H), 3.76 (s, 6H), 6.62 (s, 4H), 6.68 (s, 2H), 6.94 (d, J=9 Hz, 2H), 7.07 (d, J=9 Hz, 2H)

Elementary analysis for $C_{23}H_{30}N_2O_6 \cdot 2C_4H_4O_4 \cdot H_2O$: Calcd. (%): C,54.70; H,5.92; N,4.12 Found (%): C,54.76; H,5.93; N,4.14

Crude free base as prepared in the same manner as described above is treated with maleic acid or hydrochloric acid in a usual manner, and the crystals thus obtained are recrystallized to give the corresponding acid addition salts, the solvent for recrystallization and properties of which are shown below.

(2)
1-[(4-Methoxyphenoxy)carbonylmethyl]-4-(3,4,5-trimethoxybenzyl)piperazine dimaleate Solvent for recrystallization: methanol
Property: colorless crystals
M.p. 160°–164° C.

NMR (DMSO-d$_6$) δ: 2.8–3.3 (m, 8H), 3.68 (s, 5H), 3.75 (s, 3H), 3.81 (s, 6H), 4.24 (s, 2H), 6.16 (s, 4H), 6.84 (s, 2H), 6.95 (d, J=9 Hz, 2H), 7.09 (d, J=9 Hz, 2H)

Elementary analysis for $C_{23}H_{30}N_2O_6 \cdot 2C_4H_4O_4$: Calcd. (%): C,56.19; H,5.78; N,4.23 Found (%): C,56.07; H,5.70; N,4.21

(3)
1-[(4-Methoxyphenoxy)carbonylmethyl]-4-(3,4,5-trimethoxybenzyl)piperazine dihydrochloride Solvent for recrystallization: methanol
Property: colorless crystals
M.p. 218°–223° C. (decomp.)

NMR (DMSO-d$_6$) δ: 3.3–3.7 (m, 8H), 3.68 (s, 3H), 3.76 (s, 3H), 3.82 (s, 6H), 4.30 (br, 2H), 4.34 (br, 2H), 6.98 (d, J=9 Hz, 2H), 7.12 (s, 2H), 7.16 (d, J=9 Hz, 2H)

Elementary analysis for $C_{23}H_{30}N_2O_6 \cdot 2HCl$: Calcd. (%): C,54.88; H,6.41; N,5.56 Found (%): C,54.70; H,6.68; N,5.49

Besides, the purified free base is prepared as follows.

(4)
1-[(4-Methoxyphenoxy)carbonylmethyl]-4-(3,4,5-trimethoxybenzyl)piperazine (free base)

The 1-[(4-methoxyphenoxy)carbonylmethyl]-4-(3,4,5-trimethoxybenzyl)piperazine dihydrochloride (8.0 g) obtained above is added to a 5% aqueous potassium carbonate solution (100 ml), and the produced oily substance is extracted with chloroform (150 ml). The chloroform layer is dried over anhydrous magnesium sulfate, and the solvent is distilled off under reduced pressure. The residue is recrystallized from a mixture of ethyl acetate and n-hexane to give 1-[(4-methoxyphenoxy)carbonylmethyl]-4-(3,4,5-trimethoxybenzyl)piperazine (5.2 g).

M.p. 94°–97° C.

NMR (CDCl$_3$) δ: 2.4–2.8 (m, 8H), 3.47 (s, 4H), 3.77 (s, 3H), 3.83 (s, 3H), 3.85 (s, 6H), 6.57 (s, 2H), 6.87 (d, J=9 Hz, 2H), 7.03 (d, J=9 Hz, 2H)

Elementary analysis for $C_{23}H_{30}N_2O_6$: Calcd. (%): C,64.17; H,7.02; N,6.51 Found (%): C,64.12; H,7.06; N,6.60

EXAMPLE 3

Preparation of tablets

There are prepared compressed tablets containing as an active ingredient 1-[(4-methoxyphenoxy)carbonylmethyl]-4-(3,4,5-trimethoxybenzyl)piperazine difumarate monohydrate [compound in Example 2-(1)](100 mg per one tablet) by the following formulation.

[Formulation]

| Components | Ratio by weight |
| --- | --- |
| Compound in Example 2-(1) | 500 |
| Lactose | 100 |
| Corn starch | 300 |
| Crystalline cellulose | 80 |
| Hydroxypropyl cellulose | 10 |
| Magnesium stearate | 10 |

[Procedure]

The above components are mixed homogeneously and the mixture is tabletted in a usual manner to give tablets (200 mg per one tablet).

EXAMPLE 4

Preparation of powders

There are prepared powders containing an active ingredient 1-[(4-methoxyphenoxy)carbonylmethyl]-4-(3,4,5-trimethoxybenzyl)piperazine difumarate monohydrate [compound in Example 2-(1)] (100 mg per one pack) by the following formulation.

[Formulation]

| Components | Ratio by weight |
| --- | --- |
| Compound in Example 2-(1) | 100 |
| Lactose | 470 |
| Corn starch | 400 |
| Hydroxypropyl cellulose | 30 |

[Procedure]

The above components are mixed homogeneously and the mixture is divided and packed to give packed powders (1 g per one pack).

EXAMPLE 5

Preparation of capsules

There are prepared capsules containing as an active ingredient 1-[(4-methoxyphenoxy)carbonylmethyl]-4-(3,4,5-trimethoxybenzyl)piperazine difumarate monohydrate [compound in Example 2-(1)] (100 mg per one capsule) by the following formulation.

[Formulation]

| Components | Ratio by weight |
| --- | --- |
| Compound in Example 2-(1) | 100 |
| Lactose | 100 |
| Corn starch | 50 |
| Crystalline cellulose | 47 |
| Magnesium stearate | 3 |

[Procedure]

The above components are mixed homogeneously and the mixture is filled into #2 capsules to give capsules (300 mg per one capsule).

EXAMPLE 6

Preparation of tablets

In the same manner as described in Example 3 except that the compound in Example 1-(1) is used instead of the compound in Example 2-(1), there are prepared tablets which contain 100 mg of the compound in Example 1-(1) per one tablet.

EXAMPLE 7

Preparation of powders

In the same manner as described in Example 4 except that the compound in Example 1-(1) is used instead of the compound in Example 2-(1), there are prepared packed powders which contain 100 mg of the compound in Example 1-(1) per one pack.

EXAMPLE 8

Preparation of capsules

In the same manner as described in Example 5 except that the compound in Example 1-(1) is used instead of the compound in Example 2-(1), there are prepared capsules which contain 100 mg of the compound in Example 1-(1) per one capsule.

What is claimed is:

1. A piperazine compound of the formula:

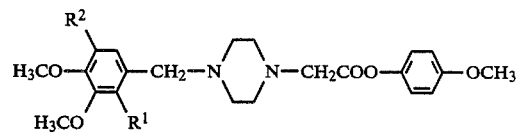

wherein either one of $R^1$ and $R^2$ is methoxy group and another is hydrogen atom, or a pharmaceutically acceptable acid addition salt thereof.

2. The compound according to claim 1, which is 1-[(4-methoxyphenoxy)carbonylmethyl]-4-(2,3,4-trimethoxybenzyl)piperazine, or a pharmaceutically acceptable acid addition salt thereof.

3. The compound according to claim 1, which is 1-[(4-methoxyphenoxy)carbonylmethyl]-4-(3,4,5-trimethoxybenzyl)piperazine or a pharmaceutically acceptable acid addition salt thereof.

4. A pharmaceutical composition for the prophylaxis and treatment of peptic ulcers, which comprises as an active ingredient a therapeutically or prophylactically effective amount of a piperazine compound of the formula:

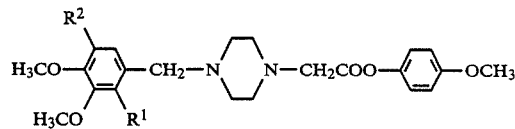

wherein either one of $R^1$ and $R^2$ is methoxy group and another is hydrogen atom, or a pharmaceutically acceptable acid addition salt thereof in admixture with a pharmaceutically acceptable carrier or diluent.

5. The pharmaceutical composition according to claim 4, wherein the active compound is 1-[(4-methoxyphenoxy)carbonylmethyl]-4-(2,3,4-trimethoxybenzyl)-piperazine or a pharmaceutically acceptable acid addition salt thereof.

6. The pharmaceutical composition according to claim 4, wherein the active compound is 1-[(4-methoxyphenoxy)carbonylmethyl]-4-(3,4,5-trimethoxybenzyl)-piperazine or a pharmaceutically acceptable acid addition salt thereof.

* * * * *

UNITED STATES PATENT AND TRADEMARK OFFICE
CERTIFICATE OF CORRECTION

PATENT NO. : 4,797,400

DATED : January 10, 1989

INVENTOR(S) : Hiroshi OHTAKA et al.

It is certified that error appears in the above-identified patent and that said Letters Patent is hereby corrected as shown below:

Item [75], line 2, change "Kenji Sukuzi" to read --Kenji Suzuki--.

Signed and Sealed this

Eleventh Day of July, 1989

Attest:

DONALD J. QUIGG

*Attesting Officer*  *Commissioner of Patents and Trademarks*